(12) United States Patent
Nestler et al.

(10) Patent No.: US 6,875,888 B2
(45) Date of Patent: Apr. 5, 2005

(54) METHOD FOR THE PRODUCTION OF ESTERS OF UNSATURATED CARBOXYLIC ACIDS

(75) Inventors: Gerhard Nestler, Ludwigshafen (DE); Jürgen Schröder, Ludwigshafen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 49 days.

(21) Appl. No.: 10/276,318

(22) PCT Filed: May 28, 2001

(86) PCT No.: PCT/EP01/06079

§ 371 (c)(1),
(2), (4) Date: Nov. 25, 2002

(87) PCT Pub. No.: WO01/92198

PCT Pub. Date: Dec. 6, 2001

(65) Prior Publication Data

US 2003/0139599 A1 Jul. 24, 2003

(30) Foreign Application Priority Data

May 29, 2000 (DE) .......................... 100 26 644

(51) Int. Cl.$^7$ .................... C07C 67/03; C07C 61/08; C07D 295/00; C07D 211/36

(52) U.S. Cl. ................. 560/217; 546/184; 546/242; 562/400

(58) Field of Search ................ 524/558, 556; 526/317.1, 319; 562/400; 560/217; 546/184, 242

(56) References Cited

U.S. PATENT DOCUMENTS

| | | | | |
|---|---|---|---|---|
| 2,129,662 A | * | 9/1938 | Barett et al. ............. | 560/222 |
| 2,406,561 A | * | 8/1946 | Rehberg ................... | 560/217 |
| 2,822,348 A | | 2/1958 | Haslam | |
| 3,686,268 A | * | 8/1972 | Jobert et al. ............. | 560/222 |
| 4,028,334 A | | 6/1977 | Chalmers | |
| 4,059,617 A | * | 11/1977 | Foster et al. ............. | 560/222 |
| 4,060,530 A | * | 11/1977 | Slejko ..................... | 556/405 |
| 4,202,990 A | * | 5/1980 | Murakami et al. ........ | 560/217 |
| 4,851,568 A | * | 7/1989 | Hurtel et al. ............. | 560/222 |
| 5,037,978 A | * | 8/1991 | Mirabelli ................. | 544/171 |
| 5,171,888 A | | 12/1992 | Roling | |
| 5,856,611 A | | 1/1999 | Schlaefer | |

FOREIGN PATENT DOCUMENTS

| | | |
|---|---|---|
| CH | 464 891 | 12/1968 |
| CH | 522 584 | 6/1972 |
| DE | 1 067 805 | 10/1959 |
| DE | 1 067 806 | 4/1960 |
| DE | 2 319 688 | 12/1973 |
| DE | 2 805 702 | 8/1978 |
| EP | 0 145 588 | 6/1985 |
| EP | 0 118 639 | 3/1987 |
| EP | 0 298 867 | 1/1989 |
| EP | 0 522 709 | 8/1996 |
| EP | 0 902 017 | 3/1999 |
| GB | 960 005 | 6/1964 |
| GB | 1 012 817 | 12/1965 |
| GB | 1 016 042 | 1/1966 |

OTHER PUBLICATIONS

E. Yoshida: "Synthesis of poly(eta–caprolactone) with a stable nitroxyl radical as an end–functional group and its application to a counter radical for living radical polymerization" Macromolecules, vol. 31, No. 5, pp. 11446–1453, Mar. 10, 1998.

* cited by examiner

Primary Examiner—Ba K. Trinh
Assistant Examiner—Taylor Victor Oh
(74) Attorney, Agent, or Firm—Oblon, Spivak, McClelland, Maier & Neustadt, P.C.

(57) ABSTRACT

In a process for preparing an ester of an unsaturated carboxylic acid by reacting an ester of the unsaturated carboxylic acid and a $C_1$–$C_4$-alkanol with an alcohol $R^3OH$, where $R^3$ is a $C_4$–$C_{20}$-alkyl radical, a $C_5$–$C_7$-cycloalkyl radical, a phenyl-$C_1$–$C_4$-alkyl radical or a $C_2$–$C_{12}$-alkyl radical substituted by at least one $NR^5R^5$ group or by from 1 to 3 hydroxyl groups or $C_1$–$C_4$-alkoxyl groups or interrupted by one or more oxygen atoms, where the radicals $R^5$ are, independently of one another, $C_1$–$C_6$-alkyl or together with the nitrogen atom form a 5- to 7-membered heterocyclic ring which may contain a further nitrogen or oxygen atom, in the presence of a transesterification catalyst, the transesterification catalyst used is at least one metal alkanolate containing at least one $OR^1$ group, where $R^1$ is a 2,2,6,6-tetraalkyl-1-oxylpiperidin-4-yl radical.

18 Claims, No Drawings

METHOD FOR THE PRODUCTION OF ESTERS OF UNSATURATED CARBOXYLIC ACIDS

BACKGROUND OF THE INVENTION

1. Field of the Invention

The present invention relates to a process for preparing an ester of an unsaturated carboxylic acid, in which an ester of the unsaturated carboxylic acid and a $C_1$–$C_4$-alkanol is reacted with an alcohol $R^3OH$ in the presence of a transesterification catalyst. The invention also relates to a metal alkoxide and the use of the metal alkoxide as transesterification catalyst in the process of the present invention.

2. Description of the Background

Among the esters of unsaturated carboxylic acids, (meth) acrylic esters are of particular industrial interest since they are valuable starting compounds for the preparation of polymers and copolymers which are employed, for example, as fibers, plastics, surface coatings, dispersions or adhesives. The term (meth)acrylic esters refers to methacrylic esters and acrylic esters. The present invention can be applied particularly advantageously to the preparation of these esters and is described below by way of example for (meth)acrylic esters. However, it can be applied generally to the transesterification of lower carboxylic esters, preferably α,β-unsaturated carboxylic esters, and particularly preferably to the transesterification of esters of unsaturated monocarboxylic acids having from 3 to 6 carbon atoms and unsaturated dicarboxylic acids having from 4 to 8 carbon atoms.

The transesterification of lower carboxylic esters with higher alcohols for preparing higher carboxylic esters in the presence of acidic or basic catalysts, in particular the preparation of (meth)acrylic esters by transesterification in the presence of acidic or basic catalysts, is generally known. In addition, it is generally known that the transesterification reaction is an equilibrium reaction. To achieve economically viable conversions, it is therefore necessary either for one of the starting materials to be used in a large excess or for at least one of the reaction products to be removed from the equilibrium, i.e. continually separated from the reaction mixture. Preference is given to separating off the product having the lowest boiling point, namely the lower alkanol liberated, which generally forms an azeotrope with the lower carboxylic ester. Accordingly, the transesterification is generally carried out by heating a mixture of the lower carboxylic ester, the higher alkanol, a catalyst and a polymerization inhibitor or inhibitor mixture to boiling and separating off the azeotrope of lower carboxylic ester and lower alkanol at the top of a distillation column which is generally located on top of the transesterification reactor.

A series of problems occur in such a case. Firstly, unsaturated carboxylic acids tend to polymerize under the action of heat or light. Particularly during the preparation and the purification by distillation, they are subjected to temperatures which can easily trigger an undesirable polymerization. The result is contamination of the apparatuses, blockage of lines and pumps and fouling of column trays and heat exchange surfaces. Cleaning of the plants is a laborious, expensive and environmentally unfriendly procedure which, in addition, greatly reduces the availability of the plants.

A further problem is the formation of by-products, e.g. of Michael addition products (addition of alkanol onto the carbon-carbon double bond), of ethers from primary alcohols and of olefins from secondary alcohols, as a result of dehydration. The secondary reactions firstly lead to losses of desired product and secondly make complicated separation and purification steps necessary.

Many of the known transesterification catalysts which are available lose activity over time. Some catalysts are so sensitive to hydrolysis that the reaction has to be carried out with careful exclusion of water, or else they decompose to form substances which require additional purification and separation steps.

Catalysts customary at present are, in particular, titanium alkoxides and zirconium alkoxides whose alkyl groups are $C_1$–$C_4$-alkyl radicals, e.g. tetramethyl, tetraethyl, tetraisopropyl, tetrapropyl, tetraisobutyl and tetrabutyl titanate (CH 522 584, CH 464 891, U.S. Pat. No. 2,822,348, EP 298 867, DE 2 319 688, GB 960 005, GB 1 012 817, GB 1 016 042, EP 145 588). However, these titanates and zirconates do not give satisfactory results since some of them are thermally unstable and extremely sensitive to hydrolysis and therefore easily lead to interfering impurities. In addition, they frequently have to be hydrolyzed to form insoluble products before they can be separated from the reaction mixture (GB 1 012 817, GB 1 016 042, U.S. Pat. No. 2,822,348).

The use of titanium tetraisopropoxide or tetrabutoxide, the most common transesterification catalysts, introduces, for example, isopropanol or butanol as impurities which generally accumulate in the unreacted lower ester which is distilled off. Owing to their boiling points and frequently also the formation of azeotropes, they are difficult to remove and can therefore lead to the formation of further by-products by means of transesterification reactions or addition onto the double bond of the esters.

Furthermore, it is known that alkyl titanates promote polymerization and can therefore give rise to formation of polymer during the preparation and work-up of the ester. This leads to a reduction in the yield, to fouling of apparatuses and to a shortening of plant running times.

Various proposals have been made for solving these problems. CH 464 891 A recommends, owing to the hydrolysis-sensitivity of the titanates, that the transesterification be carried out batchwise. In contrast to a continuous process, this enables the starting materials to be dewatered without an additional engineering outlay. However, it is disadvantageous for an industrial-scale preparation. EP 118 639 A proposes transesterification with the titanium alkoxide of the higher alkanol in the absence of the higher alkanol and in the absence of water in order to prevent the formation of azeotropes. In this process, the lower (meth)acrylic ester is reacted with the titanium alkoxide of the higher alkanol, forming the target ester together with the titanate of the lower alkanol which is, in a separate reaction step, reacted once more with the higher alkanol to form the corresponding titanate. The process is complicated and requires large amounts of titanate. It is therefore of no economic importance.

EP 298 867 A describes the transesterification of ethyl acrylate with dialkylaminoalkanols in the presence of tetraethyl titanate so as to avoid the introduction of an additional alkanol. However, methyl and ethyl titanates are expensive and, according to U.S. Pat. No. 3,686,268, are less suitable as catalysts. Owing to the thermal instability of titanates, GB 1 012 817 A proposes hydrolysis of the titanates at elevated temperature before isolation of the target ester by distillation. the formation of "lacquer deposits" in the distillation apparatus is said to be avoided in this way. Since the process includes a technically complicated filtration step and does not allow reuse of the catalyst, it is of no economic importance.

GB 1 016 042 A additionally proposes the use of a "plasticizer oil". According to U.S. Pat. No. 2,822,348, the titanate catalyst is hydrolyzed before isolation of the product by distillation or remains in the product.

To substantially avoid polymer formation, various patents and patent applications have recommended the addition of various inhibitors or inhibitor mixtures, for example aminophenols and aminomethylphenols (EP 145 588), hydroquinone, hydroquinone monomethyl ether, phenothiazine, tert-butylcatechol, methylene blue, copper sulfate or iron sulfate, alone or in admixture (EP 298 867), hydroquinone, hydroquinone monomethyl ether, phenothiazine, etc., optionally with addition of oxygen or air (CH 464 891, U.S. Pat. No. 5,037,978).

To avoid polymerization, DE 1 067 806 A proposes carrying out the transesterification under superatmospheric pressure at 180–250° C. to achieve very short residence times. Such reaction conditions require complicated apparatuses and are therefore uneconomical.

DE 1 067 805 A describes the use of quinhydrone as inhibitor and the addition of part of the lower acrylic ester required for complete transesterification only during the transesterification via the column located on top of the reactor. The process is cumbersome and requires a 3–4-fold excess of lower acrylic esters.

EP 522 709 A proposes a polymerization inhibitor composition comprising a plurality of components including an N,N'-dinitrosophenylenediamine compound, a phenothiazine and, if desired, additionally a hydroquinone, a hydroquinone monomethyl ether and/or a phenylenediamine compound.

U.S. Pat. No. 5,171,888 proposes a combination of a phenylenediamine compound and a manganese compound as polymerization inhibitor.

A further way of avoiding polymeric by-products and also for avoiding Michael additions and formation of ethers and olefins from alkanols is described in U.S. Pat. No. 5,037,978 and DE 2 805 702. U.S. Pat. No. 5,037,978 uses hafnium chelate compounds as catalysts and DE 2 805 702 uses chelate compounds of zirconium and/or calcium as catalysts.

U.S. Pat. No. 3,686,268 describes the use of titanium phenoxides as catalysts. These catalysts do not introduce any undesirable alkanols, are said to be stable to hydrolysis and reusable and additionally have a stabilizing action. The titanium phenoxides employed in U.S. Pat. No. 3,686,268 reduce the risk of polymerization, but not to an extent sufficient for the industrial transesterification of (meth) acrylic esters. They are therefore not used industrially. There is therefore a need for still further improved catalysts and processes for preparing higher esters of unsaturated carboxylic acids from their lower esters.

SUMMARY OF THE INVENTION

It is an object of the present invention to provide a process for preparing esters of unsaturated carboxylic acids with higher alcohols from their esters with lower alcohols in which the formation of undesirable by-products is reduced. A further object is to largely avoid the introduction of interfering extraneous substances.

We have found that these objects are achieved by use of a metal alkanolate which contains at least one $OR^1$ group, where $R^1$ is a 2,2,6,6-tetraalkyl-1-oxylpiperidin-4-yl radical.

The present invention accordingly provides a process for preparing an ester of an unsaturated carboxylic acid by reacting an ester of the unsaturated carboxylic acid and a $C_1$–$C_4$-alkanol with an alcohol $R^3OH$, where $R^3$ is a $C_4$–$C_{20}$-alkyl radical, a $C_5$–$C_7$-cycloalkyl radical, a phenyl-$C_1$–$C_4$-alkyl radical or a $C_2$–$C_{12}$-alkyl radical substituted by at least one $NR^5R^5$ group or by from 1 to 3 hydroxyl groups or $C_1$–$C_4$-alkoxy groups or interrupted by one or more, in particular 1, 2, 3 or 4, oxygen atoms at least two carbon atoms apart, where the radicals $R^5$ are, independently of one another, $C_1$–$C_6$-alkyl or together with the nitrogen atom form a 5- to 7-membered heterocyclic ring which may contain a further nitrogen or oxygen atom, in the presence of a transesterification catalyst comprising at least one metal alkanolate containing at least one $OR^1$ group, where $R^1$ is a 2,2,6,6-tetraalkyl-1-oxylpiperidin-4-yl radical.

DETAILED DESCRIPTION OF THE PREFERRED EMBODIMENTS

The invention further provides a metal alkanolate (hereinafter also referred to as metal alkoxide) which contains at least one $OR^1$ group, where $R^1$ is a 2,2,6,6-tetraalkyl-1-oxylpiperidin-4-yl radical.

Furthermore, the present invention provides for the use of this metal alkoxide as esterification catalyst, in particular as catalyst for transesterification.

The process of the present invention is preferably carried out in a homogeneous phase. The reaction occurs according to the following equation (I), which describes the transesterification of (meth)acrylic esters as an example:

$$H_2C=\overset{R}{\underset{|}{C}}-COOR^2 + R^3OH \rightleftharpoons$$

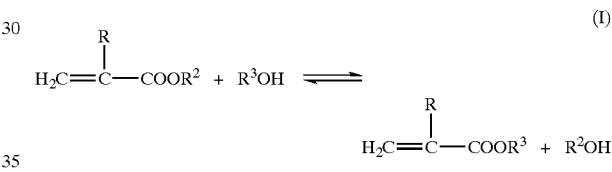

$$H_2C=\overset{R}{\underset{|}{C}}-COOR^3 + R^2OH$$

(I)

where R is H or $CH_3$, $R^2$ is $C_1$–$C_4$-alkyl and $R^3$ is as defined above. However, the process of the present invention is not restricted to acrylic esters and methacrylic esters, but is also suitable generally for saturated and unsaturated, unsubstituted and substituted monocarboxylic, dicarboxylic and polycarboxylic esters, in particular esters of α,β-unsaturated monocarboxylic acids having from 3 to 6 carbon atoms and α,β-unsaturated dicarboxylic acids having from 4 to 8 carbon atoms. The process of the present invention is particularly well suited to the transesterification of esters of acrylic acid, methacrylic acid, crotonic acid, itaconic acid, maleic acid and fumaric acid.

The alcohol component of the starting ester is an alkanol having from 1 to 4 carbon atoms ($R^2OH$), which may be linear or branched; particular preference is given to methanol and ethanol.

The starting ester is therefore preferably a methyl, ethyl, n-propyl, isopropyl or n-butyl ester.

The starting alcohol $R^3OH$ generally has a higher boiling point and/or a larger number of carbon atoms than the alcohol $R^2OH$ liberated. $R^3OH$ is preferably an alkanol having from 4 to 20 carbon atoms or an alkanol which has from 2 to 12 carbon atoms and is substituted by 1, 2 or 3 $NR^5R^5$ groups. $R^5$ are, in particular, identical or different alkyl radicals having from 1 to 4 carbon atoms. Alternatively, the radicals $R^5$ together with the nitrogen atom may form a 5- to 7-membered, saturated or unsaturated, aromatic or nonaromatic heterocyclic ring which may contain a further heteroatom, in particular N or O. Examples of such rings are pyrrolidinyl, piperidinyl, oxazolidinyl, morpholinyl, N-methylpiperazinyl, etc. The starting alcohol $R^3OH$ is particularly preferably a $C_6$–$C_{18}$-alkanol or a $C_2$–$C_6$-alkanol substituted by an $NR^5R^5$ group, with very particular preference being given to 2-di-$C_1$–$C_3$-alkylaminoethanol and in particular 2-dimethylaminoethanol.

Examples of suitable alcohols $R^3OH$ are n-butanol, isobutanol, tert-butanol, 2-ethylhexanol, 2-propylheptanol, lauryl alcohol, stearyl alcohol, cyclohexyl alcohol, cyclopentyl alcohol, dimethylaminoethanol, diethylaminoethanol, 4-dimethylaminobutan-1-ol, diethylene glycol, triethylene glycol, tetraethylene glycol, 1,4-butanediol, trimethylolpropane and benzyl alcohol.

The catalyst employed is a metal alkoxide which contains at least one $OR^1$ group, where $R^1$ is a 2,2,6,6-tetraalkyl-1-oxylpiperidin-4-yl radical. The alkyl groups may be identical or different and preferably have from 1 to 4 carbon atoms. Particular preference is given to all 4 alkyl groups being methyl groups.

Apart from at least one $OR^1$ group, the metal alkoxide may contain one or more further alkoxide groups, with the total number of groups corresponding to the valence of the metal. The further alkoxide groups can be identical or different.

Suitable metals are, in particular, titanium, zirconium, hafnium, aluminum, vanadium and alkali metals and alkaline earth metals, with preference being given to titanium, zirconium and hafnium. Most preferred are titanium alkoxides.

The metal alkoxides which are preferably used for the purposes of the present invention have the formula (II):

$$(R^1O)_bMe(OR^2)_c(OR^3)_d \qquad (II)$$

where $R^1$ is the above-mentioned 2,2,6,6-tetraalkyl-1-oxylpiperidin-4-yl radical and $R^2$ and $R^3$ are as defined above.

In formula (II) b is an integer from 1 to a, c and d are each, independently of one another, an integer from 0 to (a−1), where the sum of b, c and d corresponds to the valence a of the metal.

Particularly preferred metal alkoxides are those in which b=a, and also those in which d=0 or c=0. Most preferred are titanium, zirconium and hafnium alkoxides having from one to four 2,2,6,6-tetramethyl-1-oxylpiperidin-4-yl radicals and among these especially the titanate having four 2,2,6,6-tetramethyl-1-oxylpiperidin-4-yl radicals.

The metal alkoxides used according to the present invention can be used alone or as a mixture of a plurality of such metal alkoxides as transesterification catalysts.

The catalysts used according to the present invention can be prepared in a manner known per se by transesterification, as described, for example, in U.S. Pat. No. 3,686,268, which is hereby fully incorporated by reference. The reaction is according to the following equation (III):

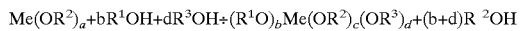

$$Me(OR^2)_a + bR^1OH + dR^3OH \rightarrow (R^1O)_bMe(OR^2)_c(OR^3)_d + (b+d)R^2OH$$

where Me, $R^1$ to $R^3$, a, b, c and d are as defined above.

The preparation is generally carried out by heating the starting metal alkoxide with the appropriate 4-hydroxy-2,2,6,6-tetraalkylpiperidine-1-oxyl compound and, if desired, a further alcohol in the desired molar ratio in the presence or absence of an inert solvent. The further alcohol is preferably the parent alcohol of the target ester of the transesterification reaction for which the metal alkoxide is to be used. The parent alcohol component of the starting metal alkoxide is liberated and removed from the reaction mixture, e.g. by distillation.

The metal alkoxides of the present invention can also be prepared in a known manner from the corresponding halides of the metals Me, cf., for example, Houben-Weyl, Methoden der Organischen Chemie, Volume 6/2, pages 1 to 70 (1963).

The transesterification process of the present invention can be carried out either batchwise or continuously. In the continuous transesterification, the starting ester, the starting alcohol, the catalyst and any further components used, e.g. inhibitors, are, for example, allowed to run individually or as a mixture into the esterification reactor or any distillation column located on top of the reactor. A customary transesterification reactor, which may be fitted with a stirrer and a heating facility for introducing the required heat of reaction, is used. The lower alcohol liberated during the course of the transesterification is removed from the reaction mixture, e.g. by distillation. The alcohol liberated is frequently removed from the reaction mixture as an azeotropic mixture with the starting ester. The target ester formed, possibly together with unreacted starting ester, remains as residue. The residue (bottom product) is passed to further work-up. In general, the bottom product is fractionated in a second distillation column where the target ester is obtained as distillate. The catalyst, any inhibitor used and polymerization products remain as residue. The residue can be partly or wholly returned to the reactor. The mixture which distills off (low boilers) can be returned to the reactor for preparing the starting ester.

Apparatuses for carrying out transesterification processes are generally known. An example of an apparatus which can be used is described in DE 23 19 688. This publication also describes a suitable way of carrying out the process.

In the process of the present invention, starting alcohol and starting ester are used in a molar ratio of from 2:1 to 1:10, preferably 1:1–5. The amount of catalyst used is preferably from 0.1 to 10% by weight, particularly preferably from 0.5 to 3% by weight, based on the reaction mixture of starting ester and starting alcohol. The reaction is carried out at customary transesterification temperatures, preferably at from about 80 to 120° C., depending on the reactants. The preferred reaction pressure is atmospheric pressure and the reaction time is generally from about 1 to 10 hours.

The metal alkoxide catalysts used according to the present invention have a stabilizing action and it is therefore possible to carry out the reaction without additional inhibitor. However, depending on the reactants and reaction conditions, it may be useful to add an inhibitor or an inhibitor mixture. Inhibitors suitable for this purpose are, for example, the known polymerization inhibitors such as hydroquinone, hydroquinone monomethyl ether, di-tert-butylcatechol, phenothiazine, p-phenylenediamine, methylene blue and indoline, either alone or as a mixture of two or more inhibitors. The preferred inhibitor is phenothiazine. Inhibitors are used in an amount of preferably from 0.001 to 1% by weight, based on the reaction mixture.

Owing to the stabilizing action of the catalysts used according to the present invention, polymer formation, which is a perennial problem in the transesterification of unsaturated carboxylic acids, is largely prevented. The apparatuses used remain free of polymeric residues over a long period of time, so that downtimes caused by cleaning work can be avoided. Losses of desired product due to undesirable secondary reactions are largely avoided. When using the catalysts employed according to the present invention, it is not necessary to carry out the reaction in the absence of water, since they are very resistant to hydrolysis. In conjunction with their excellent thermal stability, this guarantees that no interfering extraneous substances which would have to be separated off with expenditure of time and money are introduced. The composition and activity of the alkoxide catalysts used according to the present invention remain essentially unchanged during the transesterification reaction and the catalysts can be reused repeatedly. Separating them off from the reaction products is unproblematical and can be achieved by simply distilling off the target ester and any other relatively volatile components present. The metal alkoxide remains in the distillation residue which otherwise consists essentially of polymeric by-products. Since only a very small amount of polymeric by-products is formed, it is generally not necessary to carry out any further separation and the metal alkoxide can be recirculated without further purification to the reaction or be used for a new transesterification batch.

The invention illustrated but not restricted by the following examples.

EXAMPLE 1
Polymerization of N-butyl Acrylate

In a 500 ml round-bottom glass flask, 300 g of n-butyl acrylate stabilized with 15 ppm of hydroquinone monomethyl ether were heated to 100° C. and held at this temperature. The temperature of the contents of the flask was measured continuously and the temperature curve was recorded by means of a recorder. When polymerization commenced, a distinct, sudden temperature increase occurred. The time until commencement of the polymerization was determined (induction time). The procedure was repeated using a mixture of stabilized n-butyl acrylate and 0.5% of titanium tetraisopropoxide.

The induction time in the case of butyl acrylate was 43 hours, after addition of the titanate only 30 hours.

EXAMPLE 2

The induction times when 15 ppm of the titanate of hydroquinone monomethyl ether (U.S. Pat. No. 3,686,268) and of 4-hydroxy-2,2,6,6-tetramethylpiperidin-N-oxyl (cf. Example 3) were added were determined as described in Example 1. They were 54 and 100 hours, respectively.

As can be seen from Examples 1 and 2, the titanium tetraisopropoxide catalyst considerably reduces the induction time for the polymerization of butyl acrylate, while the catalyst based on hydroquinone monomethyl ether increases the induction time. However, by far the best result is achieved when the catalyst used according to the present invention is added. The risk of polymerization during the transesterification is thus considerably reduced when using the catalysts of the present invention.

EXAMPLE 3
Preparation of Tetra-2,2,6,6-tetramethyl-N-oxylpiperidin-4-yl Titanate A mixture of isopropyl titanate and 4-hydroxy-2,2,6,6-tetramethylpiperidin-N-oxyl (molar ratio=1:4) was heated at 80° C. for 3 hours and the isopropanol formed was subsequently distilled off under reduced pressure (20 mbar). The residue, which solidified when cold, comprises, according to elemental analysis, 6.6% of Ti (theoretical: 6.54%), 7.61% of N (theoretical: 7.65%), 58.9% of C (theoretical: 59.01%) and 9.5% of H (theoretical: 9.29%).

EXAMPLE 4
Preparation of N,N-dimethylaminoethyl Acrylate from Ethyl acrylate In a stirred reactor provided with superposed distillation column (100 cm, 0.5 cm Raschig rings) and condenser a mixture of 223 g of dimethylaminoethanol, 500 g of ethyl acrylate ($H_2O$ content=0.02% by weight), 20.3 g of catalyst from Example 3 and 0.01 g of phenothiazine was heated to boiling under atmospheric pressure while stirring. The reaction temperature rose from 105° C. to 130° C. during the reaction time (3.5 hours). A mixture of ethanol and ethyl acrylate was taken off at the top of the column. The reflux ratio was initially 1:1 and was increased after 3 hours to 5:1. 230 g of distillate were separated off. After the transesterification was complete, the reaction mixture was subjected to a simple vacuum distillation (25 mbar, final temperature of 120° C.). 475 g of distillate (349 g of dimethylaminoethyl acrylate, 126 g of ethyl acrylate) were obtained. The distillation residue, mainly catalyst, inhibitor and polymers, amounted to 28 g. According to analysis of the distillate by gas chromatography, a yield of 97.5%, based on the alcohol, was achieved.

EXAMPLE 5

The procedure of Example 4 was repeated, but 7.8 g of isopropyl titanate were used as catalyst. The residue amounted to 48 g and the corresponding yield was 94%.

EXAMPLE 6

Example 4 was repeated, but the residue from Example 4 was used as catalyst. The reaction proceeded in a similar manner to Example 4. 30 g of distillation residue were obtained.

As can be seen from Examples 4, 5 and 6, significantly smaller amounts of polymeric residues are obtained when using the catalyst of the present invention than when using the conventional isopropyl titanate catalyst. The catalyst of the present invention can be reused directly, without separating off the polymeric reaction products, for a new reaction.

EXAMPLE 7
Preparation of Tetra-2,2,6,6-tetramethyl-N-oxylpiperidin-4-yl Zirconate A mixture of zirconium n-propoxide and 4-hydroxy-2,2,6,6-tetramethylpiperidin-N-oxyl (molar ratio=1:4) was heated at 80° C. for 3 hours and the propanol formed was subsequently distilled off under reduced pressure (20 mbar). The residue comprised, according to elemental analysis, 11.8% of Zr (theoretical: 11.71%), 7.0% of N (theoretical: 7.19%), 55.5% of C (theoretical: 55.45%).

EXAMPLE 8
Preparation of Dimethylaminoethyltris-2,2,6,6-tetramethyl-N-oxylpiperidin-4-yl Titanate A mixture of tetramethyl titanate, 4-hydroxy-2,2,6,6-tetramethylpiperidin-N-oxyl and dimethylaminoethanol (molar ratio=1:3:1) was heated at 80° C. for 3 hours and the methanol formed was distilled off. The residue comprised, according to elemental analysis, 7.6% of Ti (theoretical: 6.4%), 8.4% of N (theoretical: 8.6%), 57.3% of C (theoretical: 57.06%).

EXAMPLE 9
Preparation of N,N-dimethylaminoethyl Acrylate

The procedure of Example 4 was repeated, but using 20 g of dimethylaminoethyltris-2,2,6,6-tetramethyl-N-oxylpiperidin-4-yl titanate.

The residue amounted to 29 g and the yield was 97%.

We claim:
1. A process for preparing an ester of an unsaturated carboxylic acid, comprising:

reacting an ester of the unsaturated carboxylic acid and a $C_1$–$C_4$-alkanol with an alcohol $R^3OH$, where $R^3$ is a $C_4$–$C_{20}$-alkyl radical, a $C_5$–$C_7$-cycloalkyl radical, a phenyl-$C_1$–$C_4$-alkyl radical or a $C_2$–$C_{12}$-alkyl radical substituted by at least one $NR^5R^5$ group or by from 1 to 3 hydroxyl groups or $C_1$–$C_4$-alkoxyl groups or interrupted by one or more oxygen atoms, where the radicals $R^5$ are, independently of one another, $C_1$–$C_6$-alkyl or together with the nitrogen atom form a 5- to 7-membered heterocyclic ring which may contain a further nitrogen or oxygen atom, in the presence of a transesterification catalyst comprising at least one metal alkanolate that has at least one $OR^1$ group, where $R^1$ is a 2,2,6,6-tetraalkyl-1-oxylpiperidin-4-yl radical, and wherein the metal of the metal alkanolate is at least metal selected from the group consisting of titanium, zirconium, hafnium, aluminum, vanadium, an alkali metal or of an alkaline earth metal.

2. The process as claimed in claim 1, wherein the unsaturated carboxylic acid is an α,β-ethylenically unsaturated monocarboxylic acid having from 3 to 6 carbon atoms or a dicarboxylic acid having from 4 to 8 carbon atoms.

3. The process as claimed in claim 1, wherein the unsaturated carboxylic acid is acrylic acid or methacrylic acid.

4. The process as claimed in claim 1, wherein the metal alkanolate is selected from the group consisting of metal alkoxides of titanium, zirconium and hafnium.

5. The process as claimed in claim 1, wherein the alcohol $R^3OH$ is one in which $R^3$ is a $C_2$–$C_6$-alkyl radical which is substituted by an $NR^5R^5$ group and the radicals $R^5$ are, independently of one another, $C_1$–$C_3$-alkyl.

6. The process as claimed in claim 1, wherein the transesterification catalyst comprises at least one metal alkanolate of the formula (II)

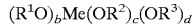

where $R^1$ is a 2,2,6,6-tetraalkyl-1-oxylpiperidin-4-yl radical, $R^2$ is a $C_1$–$C_4$-alkyl radical, $R^3$ is a $C_4$–$C_{20}$-alkyl radical, a $C_5$–$C_7$-cycloalkyl radical, a phenyl-$C_1$–$C_4$-alkyl radical or a $C_2$–$C_{12}$-alkyl radical which is substituted by at least one $NR^5R^5$ group or by from 1 to 3 hydroxyl groups or $C_1$–$C_4$-alkoxyl groups or interrupted by one or more oxygen atoms, where the radicals $R^5$ are, independently of one another, $C_1$–$C_6$-alkyl or together with the nitrogen atom form a 5- to 7-membered heterocyclic ring which may contain a further nitrogen or oxygen atom, Me is Ti, Zr, Hf, Al, V, an alkali metal or an alkaline earth metal, wherein a is the valence of the metal, b is an integer from 1 to a, c and d are each, independently of one another, an integer from 0 to (a−1), and b+c+d=a.

7. The process as claimed in claim 6, wherein the metal alkanolate is present in an amount ranging from 0.1 to 10% by weight, based on the reaction mixture of ester and alcohol $R^3OH$.

8. A metal alkanolate that has at least one $OR^1$ group, where $R^1$ is a 2,2,6,6-tetraalkyl-1-oxylpiperidin-4-yl radical, and wherein the metal of the alkanolate is at least one metal selected from the group consisting of titanium, zirconium, hafnium, vanadium or an alkaline earth metal.

9. The metal alkoxide as claimed in claim 8, wherein the alkanolate is of titanium, zirconium or hafnium.

10. The metal alkanolate as claimed in claim 8 having the formula (II):

where $R^1$ is a 2,2,6,6-tetraalkyl-1-oxylpiperidin-4-yl radical, $R^2$ is a $C_1$–$C_4$-alkyl radical, $R^3$ is a $C_4$–$C_{20}$-alkyl radical, a $C_3$–$C_7$-cycloalkyl radical, a phenyl-$C_1$–$C_4$-alkyl radical or a $C_2$–$C_{12}$-alkyl radical which is substituted by at least one $NR^5R^5$ group or by from 1 to 3 hydroxyl groups or $C_1$–$C_4$-alkoxyl groups or interrupted by one or more oxygen atoms, where the radicals $R^5$ are, independently of one another, $C_1$–$C_6$-alkyl or together with the nitrogen atom form a 5- to 7-membered heterocyclic ring which may contain a further nitrogen or oxygen atom, wherein a is the valence of the metal, Me is Ti, Zr, Hf or an alkaline earth metal, b is an integer from 1 to a, c and d are each, independently of one another, an integer from 0 to (a−1), and b+c+d=a.

11. The metal alkanolate as claimed in claim 10 having formula (II), in which Me is Ti or Zr, and $R^1$ is the 2,2,6,6-tetraalkyl-1-oxylpiperidin-4-yl radical, b is 4 and c and d are each 0.

12. The process as claimed in claim 1, a wherein the starting alcohol and the starting ester are combined in a molar ratio of 2:1 to 1:10.

13. The process as claimed in claim 1, wherein the catalyst is employed in an amount ranging from 0.1 to 10% by weight based on the weight of the reaction mixture of the starting alcohol and the starting ester.

14. The process as claimed in claim 13, wherein the catalyst is employed in an amount ranging from 0.5 to 3% by weight based on the weight of the reaction mixture of the starting alcohol and the starting ester.

15. The process as claimed in claim 1, wherein the transesterification reaction is conducted at a temperature of 80 to 120° C.

16. The process as claimed in claim 1, wherein the transesterification reaction is conducted in the presence of an inhibitor that is present in an amount ranging from 0.001 to 1% by weight, based on the reaction mixture.

17. The process as claimed in claim 13, wherein the inhibitor is hydroquinone, hydroquinone monomethyl ether, di-tert-butylcatechol, phenothiazine, p-phenylenediamine; methylene blue or indoline.

18. The process as claimed in claim 1, wherein the catalyst is $Ti(OR^1)_4$ in which all four $R^1$ groups are the 2,2,6,6-tetraalkyl-1-oxylpiperidin-4-yl radical.

* * * * *